United States Patent [19]

Wild

[11] Patent Number: 4,892,966
[45] Date of Patent: Jan. 9, 1990

[54] ACETOACETIC ACID ESTER DERIVATIVES FOR THE MANUFACTURE OF α-HYDROXYCARBONYL COMPOUNDS

[75] Inventor: Hans J. Wild, Wolfhausen, Switzerland

[73] Assignee: Givaudan Corporation, Clifton, N.J.

[21] Appl. No.: 86,130

[22] PCT Filed: Nov. 13, 1986

[86] PCT No.: PCT/CH86/00157
§ 371 Date: Jul. 16, 1987
§ 102(e) Date: Jul. 16, 1987

[87] PCT Pub. No.: WO87/03287
PCT Pub. Date: Jun. 4, 1987

[30] Foreign Application Priority Data

Nov. 20, 1985 [CH] Switzerland ............... 4942/85
Sep. 23, 1986 [CH] Switzerland ............... 3805/86

[51] Int. Cl.$^4$ .................................. C07C 69/716
[52] U.S. Cl. .................................. 560/174; 260/408; 260/410.9 R; 131/276; 426/538; 512/8; 568/346; 568/379; 568/380
[58] Field of Search ........... 560/174; 260/408, 410.9 R

[56] References Cited

U.S. PATENT DOCUMENTS 2,387,587 1/1939 Hunsdiecker .
3,180,893 4/1965 Robinson et al. .
3,405,163 10/1968 Bambury et al. ............... 560/174
3,907,896 9/1975 Calame et al. .
4,025,537 5/1977 Kretchmer et al. ............... 560/174
4,384,144 5/1983 Shono et al. .

FOREIGN PATENT DOCUMENTS 0080600 6/1983 European Pat. Off. .
0076378 1/1985 European Pat. Off. .
2360679 6/1974 Fed. Rep. of Germany .
2347329 11/1977 France .
562191 5/1975 Switzerland .
576411 6/1976 Switzerland .
2041935 9/1980 United Kingdom .

OTHER PUBLICATIONS

G. M. Strunz, J. Agric. Food Chem. 31 (1983) 185–190.
S. Arctander, "Perfume and Flavor Chemicals", II, Montclair, N.J. (1969) #1987.
J. Arnarp et al., Acta Chem. Scan. B40 (1986).
Chemical Abstracts, (1980) 92:75957a for JP-A-79103842.
T. Kato et al.; J.C.S. Perkin I (1979) 529–532.
M. Fedorynski et al.; J. Org. Chem. 43 (1978) 4682–4684.

Primary Examiner—Vivian Garner
Attorney, Agent, or Firm—Robert F. Tavares; Linda A. Vag

[57] ABSTRACT

The invention is concerned with a novel process for the manufacture of compounds of the formula

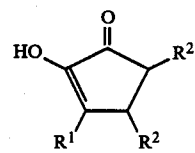

I wherein $R^1$ signifies $C_{1-5}$-alkyl, especially methyl, ethyl, propyl or isopropyl, and the radicals $R^2$ each independently represent hydrogen or $C_{1-5}$-alkyl, especially hydrogen or methyl, ethyl, propyl or isopropyl.

The process is characterized in that a compound of the formula

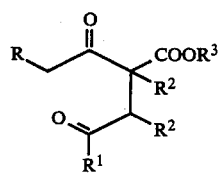

II wherein R stands for $C_{1-4}$-alkoxy, chlorine, bromine or $C_{1-4}$-alkanoyloxy, $R^1$ and $R^2$ have the above significance and $R^3$ represents $C_{1-4}$-alkyl.

is hydrolyzed and subjected to an aldol condensation and, where R=$C_{1-4}$-alkoxy, the reaction product is subsequently subjected to an acid treatment.

The compounds I are for the most part known flavoring substances.

8 Claims, No Drawings

ACETOACETIC ACID ESTER DERIVATIVES FOR THE MANUFACTURE OF α-HYDROXYCARBONYL COMPOUNDS

The invention is concerned with a novel process for the manufacture of α-hydroxycarbonyl compounds, especially those of the formula

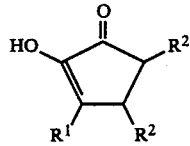  I wherein $R^1$ signifies $C_{1-5}$-alkyl, especially methyl, ethyl, propyl or isopropyl, and the radicals $R^2$ each independently represent hydrogen or $C_{1-5}$-alkyl, especially hydrogen or methyl, ethyl, propyl or isopropyl.

The process in accordance with the invention is characterized in that a compound of the general formula

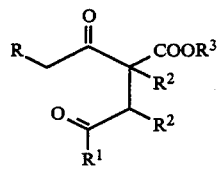  II wherein R stands for $C_{1-4}$-alkoxy, chlorine, bromine or $C_{1-4}$-alkanoyloxy, e.g. acetoxy, propionyloxy, butyryloxy, $R^1$ and $R^2$ have the above significance and $R^3$ represents $C_{1-4}$-alkyl, is hydrolyzed and subjected to an aldol condensation.

In this alkaline hydrolysis the ester bonds which are present in II (R in II=$C_{1-4}$-alkanoyloxy and the group —COOR$^3$) are cleaved. The aldol condensation yields the compound I.

Where R=chlorine or bromine, only the group —COOR$^3$ is initially cleaved hydrolytically and, after the aldol condensation has been carried out, the halogen residue R must also be hydrolyzed alkalinically.

As the aldol condensation is preferably carried out alkalinically, where R=$C_{1-4}$-alkoxy the compound

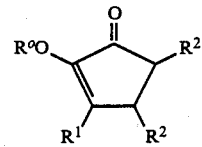  I' wherein R° stands for $C_{1-4}$-alkyl and $R^1$ and $R^2$ have the above significance, which is initially formed in this manner must, of course, thereupon be subjected to an acidic ether cleavage.

Tautomerism is possible where $R^1 \neq R^2 \neq H$. Formula I is accordingly intended to embrace both tautomeric forms and their mixtures.

The convenient parameters for the process in accordance with the invention, i.e. the conversion in accordance with the invention of II into I, are indicated in the following Reaction Scheme and Table I relating thereto.

Moreover, this Scheme and Table I contain the convenient parameters for the process for the preparation of the compounds II.

In this Scheme:
R°=$C_{1-4}$-alkyl, e.g. as given above,
Me=alkali metal, e.g. Na, K,
AcO=$C_{1-4}$-alkanoyloxy, e.g. as given above,
X=Cl, Br.

The novel compounds II are obtained by alkylating a compound of the formula

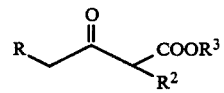  III wherein R, $R^2$ and $R^3$ have the above significance, conveniently by means of halocarbonyl compounds in accordance with the Reaction Scheme.

In a particular embodiment in the case of $R^2$=$C_{1-5}$-alkyl ($R^2$ in the α-position to the ester group) a corresponding compound III is not used, but the compound of formula II is alkylated prior to its hydrolysis and the aldol condensation which are conveniently carried out without separating the alkylated product.

Reaction Scheme

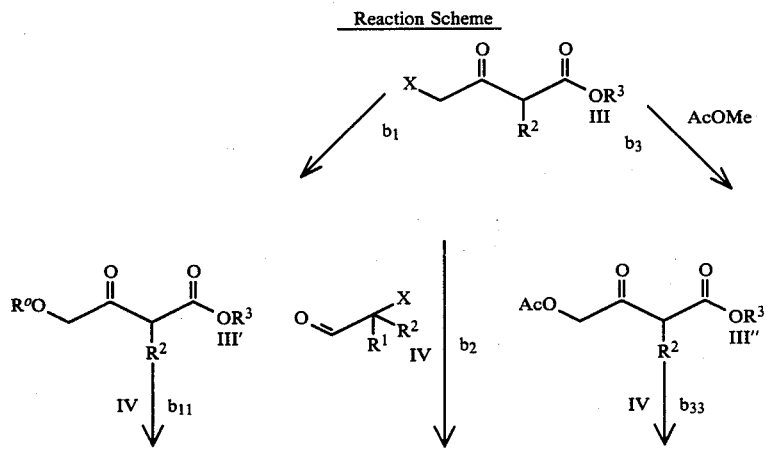

-continued

Reaction Scheme

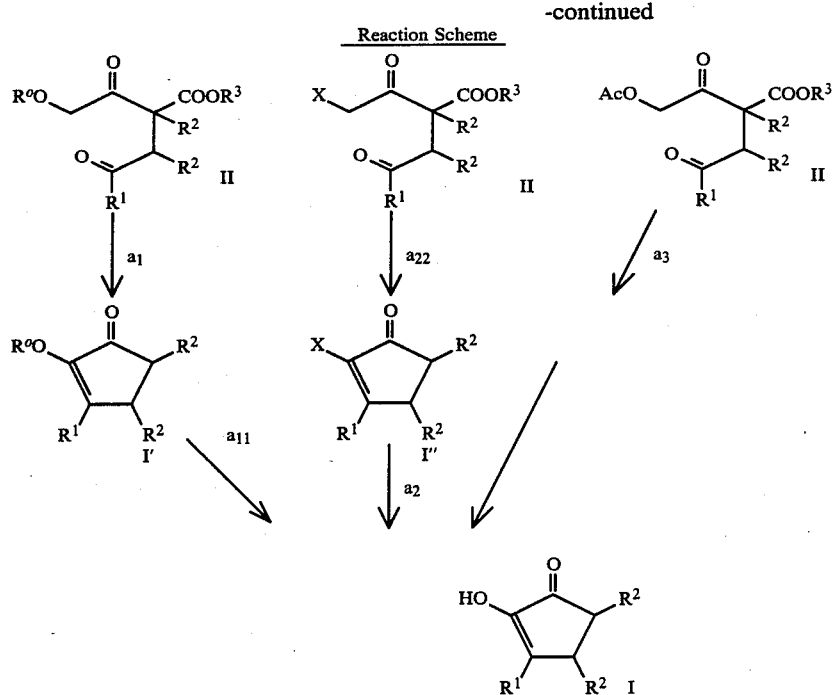

Table I provides information concerning convenient methods and reagents as well as convenient and preferred reaction parameters for the individual process steps.

TABLE 1

| Step | Type of reaction | Reagent | T | Literature |
|---|---|---|---|---|
| a 1<br>a 3 | Hydrolysis (1) alkaline (ester cleavage) concomitant aldol condensation | Metal hydroxides, metal carbonates, metal bicarbonates in aqueous solution | 20–100° C. | H.O. House, Modern Synthetic Reactions, 2nd ed. W. A. Benjamin Inc. Menl. Park, California, 1972, 511 seq., 629 seq. |
| a 11 | Enol-ether cleavage (1) | Strong acids e.g. $H_2SO_4$, HCl, $H_3PO_4$ aqueous solution; HI, HBr/$CH_3COOH$ | Reflux temperature | H.O. House loc, cit. 504 |
| a 2 | Hydrolysis (1) | Alkaline conditions: Metal hydroxides, e.g. alkali metal hydroxides, alkaline earth metal hydroxides, preferably in aqueous solution. aqueous ammonia solution | 20–100° C. | |
| a 22 | Hydrolysis (1) alkaline (ester cleavage) concomitant aldol condenation | Weakly basic: Metal carbonates, metal bicarbonates in aqueous solution | 20–100° C. | H.O. House, loc. cit., 511 seq., 629 seq. |
| b 1 | Substitution (alkoxylation) | Alkali alcoholate in excess: aprotic solvent, e.g. acetonitrile, propionitrile, etc. | preferably 50–100° C. | EP-PS 76,378 CH-PS 562,191 |
| b 3 | Substitution (acyloxylation) | Reaction with a metal alkanoate in polar aprotic solvents, e.g. $CH_3CN$, DMF, DMSO, acetone, sulpholane, with III being conveniently added slowly to the metal alkanoate | 50–100° C. | Kato et al. J. C. S. Perkin I, (1979), 529 |
| b 11, b 2, b 33 | Condensation (oxalkylation) | Weakly basic medium; especially by means of alkali carbonates or alkali bicarbonates or by means of trialkylamines, | 20–100° C. | Fedorynski et al., J. Org. Chem. 43 (24), 4682 (1978) |

TABLE 1-continued

| Step | Type of reaction | Reagent | T | Literature |
|------|------------------|---------|---|------------|
| | | e.g. triethylamine, preferably in the presence of tetraalkyl-ammonium salts or crown ethers as catalysts. in polar solvents, e.g. CH₃CN, DMF, DMSO, acetone, sulpholane; or in water; or also in the absence of solvent III or III′ or III″: IV = 1:1-3, esp. 1:1-1.5 | | |
| | Alkylation of II (basic, non-aqueous) | Alkyl halides/metal carbonates, e.g. alkyl iodides/metal carbonates, metal alcoholates in aprotic solvents, e.g. acetonitrile, DMF, DMSO | 20–80° C. | Organikum, organisch-praktisches Grundpraktikum, collective authors, VEB, deutscher Verlag der Wissenschaften, Berlin, 1967, pages 469 et seq. |

(1) According to methods known per se

The compounds of formula I are for the most part known. They are odorant and/or flavouring substances, whereby in this respect the following compounds stand in the foreground of interest:

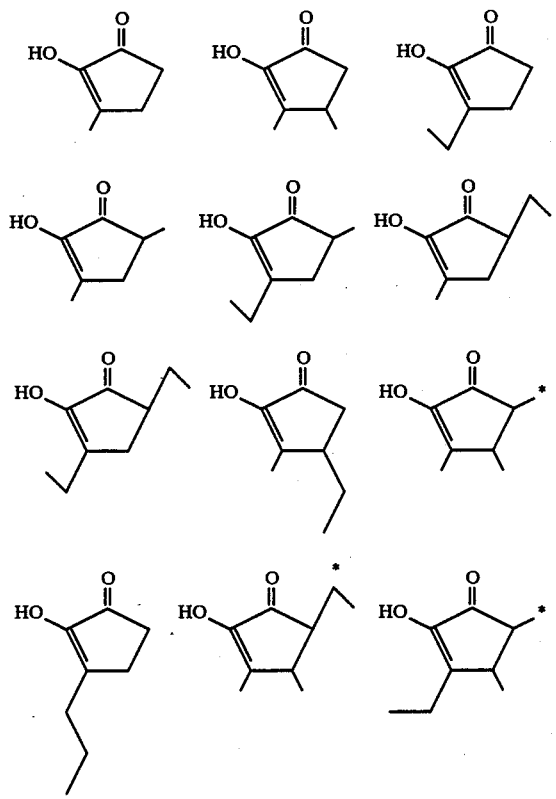

The compounds marked with asterisks as novel; these compounds are also an object of the present invention, as are odorant and/or flavouring substance compositions containing the novel compounds and the use of the novel compounds as odorant and/or flavouring substances.

The organoleptic properties of the novel compounds are as follows:

| | Odour[1] | Flavour[2] |
|---|---|---|
| 2-Hydroxy-3,4,5-trimethyl-2-cyclopenten-1-one | sweet, burnt, powerful, corylone-like, after caramel, maple | sweet, burnt, spicy, corylone-like, after caramel, maple, coffee, bread, liquorice |
| 5-Ethyl-2-hydroxy-3,4-dimethyl-2-cyclopenten-1-one + tautomeric form 2-Hydroxy-3,4,4-trimethyl-2-cyclopenten-1-one | burnt, spicy, powerful, after caramel, coffee, nuts weaker by twice than above | very similar to that above |

[1] 10% in C₂H₅OH
[2] 3 ppm in H₂O

A comparison of the novel trimethyl derivative with the most well known of the above flavouring substances, 2-hydroxy-3-methyl-2-cyclopenten-1-one ("Corylone"), see S. Arctander, Perfume and Flavor Chemicals, Montclair N.J. 1969; indicated that in the first case the flavour intensity is 20 times greater (measured in both instances in water, c=1-10 ppm).

Compared with the known, structurally related odorant substance 2-hydroxy-3,4,4-trimethyl-2-cyclopenten-1-one (Eu-A 80 600), only the novel trimethyl derivative produces surprising effects in compositions of the fougère, rose, tobacco and leather type.

The novel compounds of formula I used in accordance with the invention as odorant and/or flavouring substances enrich the olfactory character of odorant substance compositions, especially of fougère-like, chypre-like, woody, animal compositions or bases. The compounds I combine with numerous known odorant substance ingredients of natural of synthetic origin, whereby the range of the natural raw substances can embrace not only readily volatile but also moderately volatile and difficulty ("slightly") volatile components and that of the synthetics can embrace representatives from practically all classes of substances, as is evident from the following compilation:

Natural products: Basil oil, tree moss absolute, mugwort oil, bergamot oil, cassis bud absolute, castoreum, cedarwood oil, ciste labdanum, civet, coriander oil, oak moss, elemi oil, pine needle oil, galbanum, geranium oil, clove oil, jasmin absolute and its synthetic substitute, jonquille absolute, camomile oil, labdanum, lavender oil, mandarin oil, mastix absolute, mentha citrata oil, myrrh oil, palmarosa oil, patchouli oil, petitgrain oil Paraguay, sandalwood oil, thyme oil, vassoura oil, musk infusion, styrax, birch tar, vetiver oil, frankincense, ylang-ylang oil, lemon oil, civet oil, etc.

Alcohols: Citronellol, Dimetol® (3,6-dimethyl-heptan-2-ol), geraniol, cis-3-hexenol, linalool, Nonadyl® (6,8-dimethyl-nonan-2-ol), phenylethyl alcohol, rhodinol, Sandela® (3-isocamphyl -5-cyclohexanol), Sandalore® (3-methyl-5-(2',2',3'-trimethyl-cyclopent-3'-en-1'-yl)-pentan-2-ol), terpineol, etc.

Aldehydes: α-Amylcinnamaldehyde, cyclamen aldehyde, decanal, dodecanal, heliotropin, α-hexylcinnamaldehyde, hydroxycitronellal, lyral, Adoxal® (2,6,10 -trimethyl-undec-9-en-1-al), undecanal, ω-undecylene aldehyde, vanillin, etc.

Ketones: Isoraldeine® (isomethyl-α-ionone), α-ionone, β-ionone, 3-prenylisocaranone, Vertofix® (=acetylated cedarwood oil), p-methylacetophenone, etc.

Esters: Ethyl acetoacetate, amyl salicylate, benzyl acetate, cedryl acetate, cinnamyl formate, citronellyl acetate, geranyl acetate, cis-3-hexenyl acetate, cis-3-hexenyl benzoate, linalyl acetate, linalyl anthranilate, methyl dihydrojasmonate, Methambrat® (1-acetoxy-1-methyl-2-sec. -butylcyclohexane), Myraldylacetat® (4-(4-methyl-3-pentenyl)-cyclohex-3-en-1-yl-carbinyl acetate), phenoxyethyl isobutyrate, phenylethyl tiglate, styrallyl acetate, terpenyl acetate, 2,3,6,6-tetramethyl-cyclohex-2-ene-carboxylic acid ethyl ester, 3,6,6-trimethyl-2-ethyl-cyclohex-2-ene-carboxylic acid ethyl ester, vetivenyl acetate, ortho-tert.butylcyclohexyl acetate, etc.

Various: Musk ambrette, coumarin, epoxycedrene, eugenol, Fixolide® (1,1,2,4,4,7-hexamethyl-6-acetyl-1,2,3,4-tetrahydronaphthalene), Galaxolid® (1,3,4,6,7,8-hexahydro-4,6,6,7,7,8-hexamethyl-cyclopenta-γ-2-benzopyran), heliotropin, indole, indolene, isoeugenol, isobutylquinoline, jasmonyl (1,3-diacetoxy-nonane), musk ketone, limonene, p-menthane-8-thiol-3-one, Madrox® (1-methylcyclododecyl methyl ether), methyleugenol, Musk 174® (12-oxahexadecanolide), γ-nonalactone, γ-undecalactone, etc.

The compounds of formula I (or their mixtures) can be used in wide limits which can extend in compositions, for example, from 0.1 (detergents) —30% (alcoholic solutions). These values are not intended to represent limiting values, as the experienced perfumer can also achieve effects with even lower concentrations or can synthesize novel complexes with even higher dosages. The preferred concentrations range between 0.1 and 25%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco, etc).

The compounds I (or their mixtures) can accordingly be used for the manufacture of compositions and, as the above compilation shows, using a wide range of known odorant substances or odorant substance mixtures. In the manufacture of such compositions the odorant substances or odorant substance mixtures mentioned above can be used according to methods known to the perfumer, such as e.g. according to W. A. Poucher, Perfumes, Cosmetics, Soaps 2, 7th Edition, Chapman and Hall, London 1974.

The novel compounds of formula I are also excellently suited for use in flavours of the widest variety of kinds, but especially for the flavouring of tobacco.

As flavouring substances the compounds I can be used, for example, for the production or improvement, intensification, enhancement or modification of fruit flavours, e.g. blueberry or blackberry flavours, of walnut, hazelnut, almond, chocolate, coffee and milk flavours, etc. As fields of use for these flavours their come into consideration, for example, foodstuffs (yoghurt, confectionery etc.), semi-luxury consumables ("Genussmittel") (tea, tobacco, etc.) and drinks (lemonade etc.).

The pronounced flavour qualities of the compounds I enable them to be used as flavouring substances in low concentrations. A suitable dosage embraces, for example, the range of 0.01 ppm–100 ppm, preferably the range of 0.01 ppm–20 ppm, in the finished product, i.e. the flavoured foodstuff, semi-luxury consumable or drink.

In the flavouring of, for example, tobacco the dosage can, however, also lie higher and can embrace a wider range, for example the range of 1 to 1000 ppm, preferably 30–100 ppm.

The compounds can be mixed with the ingredients used for flavouring compositions or added to such flavourants in the usual manner. Under the flavourants used in accordance with the invention there are to be understood flavouring substance compositions which can be diluted or dispersed in edible materials in a manner known per se. They contain, for example, about 0.1–10, especially 0.5–3 wt.%. they can be converted according to methods known per se into the usual forms of use such as solutions, pastes or powders. The products can be spray-dried, vacuum-dried or lyophilized.

The known flavouring substances conveniently used in the manufacture of such flavourants are either already contained in the above compilation or can be concluded readily from the literature, such as e.g. J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press, Inc., Cleveland, Ohio 1975.

For the manufacture of such usual forms of use there come into consideration, for example, the following carrier materials, thickening agents, flavour improvers, spices and auxilliary ingredients, etc:

Gum arabic, tragacanth, salts or brewers' yeast, alginates, carrageen or similar absorbents; indoles, maltol, dienals, spice oleoresins, smoke flavours; cloves, diacetyl, sodium citrate; monosodium glutamate, disodium inosine-5'-monophosphate (IMP), disodium guanosine-5-phosphate (GMP); or special flavouring substances, water, ethanol, propylene glycol, glyercine.

EXAMPLE 1

(a) 113.4 g (2.1 mmol) of sodium methylate are suspended in 150 ml of acetonitrile. 150.5 g (1 mol) of methyl 4-chloroacetoacetate are thereupon allowed to flow in within 5 minutes. The temperature rises, but it is held at 68°–70° C. by cooling. The mixture is subsequently stirred at 70° C. for a further 25 minutes. The reaction mixture is poured into a solution of 350 ml of distilled water and 9 g of acetic acid and held at a pH value of 6–7 by the addition of a total of 83 ml of 32% hydrochloric acid. The organic layer is separated in a separating funnel and the aqueous layer is extracted 3 times with 200 ml of acetonitrile each time. The combined organic phases are dried over magnesium sulphate and concentrated on a rotary evaporator. The crude product distils at 55°-57° C./0.6 mbar. There are obtained 132.34 g (90.6%) of methyl 4-methoxy-acetoacetate.

IR (liq. film): 3450$^m$, 1750$^s$, 1700$^s$, 1660$^m$ cm$^{-1}$
NMR (CDCl$_3$)60MHz: 3.44 (s/3H), 3.52 (s/2H), 3.76 (s/3H), 4.10 (s/2H) ppm
MS (m/e): 146 (M+), 115, 101, 59, 45 (100%).

(b) 165.8 g (1.2 mol) of potassium carbonate and 4.6 g (0.02 mol) of benzyltriethylammonium chloride are suspended in 500 ml of acetonitrile. While stirring there are added thereto 146.1 g (1 mol) of methyl 4-methoxy-acetoacetate and there are added dropwise thereto within 10 minutes 138.8 g (1.5 mol) of chloroacetone. The mixture is stirred at 20°-25° C. for a further 7 hours. The reaction mixture is poured on to 1 liter of 10% NaH$_2$PO$_4$ solution/ice (pH value=5) and extracted 3 times with 500 ml of ethyl acetate each time. The combined organic phases are dried over magnesium sulphate and concentrated on a rotary evaporator to give 206.30 g (100%) of methyl 4-methoxy-2-acetonylacetoacetate, content: 84.3%; b.p. 104°-105° C./0.06 mbar.

IR (liq. film): 3610$^m$, 1745$^2$, 1715$^s$, 1630$^m$ cm$^{-1}$
NMR (CDCl$_3$)60MHz: 2.20 (s/3H), 3.01-3.21 (m/2H), 3.45 (s/3H), 3.73 (s/3H), 4.00-4.23 (m/1H), 4.28 (s/2H) ppm
MS (m/e): 202 (M+,) 157, 125, 97, 55, 45 (100%).

(c) 201.3 g (0.997 mol) of crude methyl 4-methoxy-2-acetonylacetoacetate are held at reflux temperature for 3 hours with 2.12 liters (0.5 mol) of 2.5% Na$_2$CO$_3$ solution. The reaction mixture is extracted 3 times with 100 ml of CH$_2$Cl$_2$ each time. The combined organic phases are dried over magnesium sulphate and concentrated on a rotary evaporator to give 99.90 g (79.5%) of 2-methoxy-3-methyl-2-cyclopenten-1-one, content 84.2%; b.p. 82°-84° C./27 mbar.

IR (liq. film): 1700$^2$, 1645$^s$ cm$^{-1}$
NMR (CDCl$_3$)60 MHz: 2.00 (s/3H), 2.40 (s/4H), 3.88 (s/3H) ppm
MS (m/e): 126 (M+, 100%), 111, 97, 83, 55.

(d) 94.8 g (0.75 mol) of crude 2-methoxy-3-methyl-2-cyclopenten-1-one are held at reflux temperature for 5 hours with 1.896 kg (20 fold amount by weight) of 5N hydrochloric acid. The reaction mixture is extracted 3 times with 300 ml of CH$_2$Cl$_2$ each time. The organic phases are extracted twice with 500 ml of 2N sodium hydroxide solution each time. The combined NaOH extracts are adjusted to a pH value of 5 with concentrated hydrochloric acid while cooling and then extracted 3 times with 300 ml of CH$_2$Cl$_2$ each time. The combined organic phases are dried over magnesium sulphate and concentrated on a rotary evaporator. After recrystallization from acetone/water 1:1 there are obtained 57.66 g (68.4%) of 2-hydroxy-3-methyl-2-cyclopenten-1-one; m.p. 100°-102° C.

IR (CHCl$_3$): 3500$^m$, 3310$^w$ (broad), 1710$^s$, 1660$^s$ cm$^{-1}$
NMR (CDCl$_3$)60 MHz: 2.02 (s/3H), 2.45 (s/4H), 7.00 (s, broad/1H) ppm
MS (m/e): 112 (M+, 100%), 97, 84, 69, 55, 41.

EXAMPLE 2

(a) 108 g (1.1 mol) of potassium acetate and 11.4 g (0.05 mol) of benzyltriethylammonium chloride are suspended in 900 ml of acetonitrile, treated with 50 ml of acetic acid and heated to reflux temperature. Within 3½ hours there are added dropwise thereto 150.5 g (1 mol) of methyl 4-chloroacetoacetate in 100 ml of acetonitrile and the mixture is subsequently held at reflux temperature for 4 hours. The reaction mixture is washed 3 times with 200 ml of 5% NaH$_2$PO$_4$ solution each time and the aqueous phases are back-extracted with 200 ml of CH$_2$Cl$_2$. The combined organic phases are dried over magnesium sulphate and concentrated on a rotary evaporator. The crude product distils at 76°-85° C./0.6 mbar and gives 106.17 g (61%) of methyl 4-acetoxyacetoacetate.

IR (liq. film): 3610-3450$^w$ (complex), 1740$^s$ (broad) 1650$^m$ (s)
NMR (CDCl$_3$)60 MHz: 2.19 (s/3H), 3.53 (s/2H), 3.78 (s/3H), 4.80 (s/2H) ppm
MS (m/e): 174 (M+), 132, 101, 74, 59, 43 (100%)

(b) 63.6 g (0.6 mol) of sodium carbonate and 2.3 g (0.01 mol) of benzyltriethylammonium chloride are suspended in 250 ml of acetonitrile. While stirring there are added thereto 87.0 g (0.5 mol) of methyl 4-acetoxyacetoacetate and there are added dropwise thereto within 5 minutes 69.4 g (0.75 mol) of chloroacetone. The mixture is stirred at 20°-25° C. for a further 46 hours. The reaction mixture is poured on to 1 liter of 10% NaH$_2$PO$_4$ solution/ice (pH value=5) and extracted 3 times with 300 ml of ethyl acetate each time. The combined organic phases are dried over magnesium sulphate and concentrated completely on a rotary evaporator to give 105.9 g (92%) of methyl 4-acetoxy-2-acetonylacetoacetate, content 76.9%; b.p. 119°-121° C./0.06 mbar.

IR (liq. film): 1730$^s$ (broad, complex) cm$^{-1}$
NMR (CDCl$_3$)60 MHz: 2.18 (s/3H), 2.21 (s/3H), 3.09-3.22 (m/2H), 3.76 (s/3H), 4.11 (t/1H), 4.97 (s/2H) ppm
MS (m/e): 170, 157, 125, 97, 87, 43 (100%).

(c) 230 mg (1 mol) of crude methyl 4-acetoxy-2-acetonylacetoacetate are held at reflux temperature for 1 hour with 2 ml (0.19 mmol) of 1% Na$_2$CO$_3$ solution, whereby the PH value drops to 6. Solid Na$_2$CO$_3$ is added thereto until the pH value remains at 11-12 and the mixture is held at reflux temperature of a further 1 hour. The reaction mixture is poured on to 10 ml of 10% NaH$_2$PO$_4$ solution/ice (pH value=5) and extracted 3 times with 20 ml of CH$_2$Cl$_2$ each time. The combined organic phases are dried with magnesium sulphate and concentrated on a rotary evaporator to give 60.2 mg (53.7%) of 2-hydroxy-3-methyl-2-cyclopenten-1-one, content: 95.7%; m.p. 100°-102° C.

IR (CHCl$_3$): 3500$^m$, 3310$^w$ (broad), 1710$^s$ 1660$^s$ cm$^{-1}$
NMR (CDCl$_3$)60 MHz: 2.02 (s/3H), 2.45 (s/4H) ppm.

EXAMPLE 3

(a) 127.2 g (1.2 mol) of sodium carbonate and 4.6 g (0.02 mol) of benzyltriethylammonium chloride are suspended in 800 ml of acetonitrile. While stirring there is added dropwise thereto within 8 hours a solution of 150.5 g (1 mol) of methyl 4-chloroacetoacetate and 138.8 g (1.5 mol) of chloroacetone in 200 ml of acetonitrile. The mixture is stirred at 20°-25° C. for a further 15 hours. The reaction mixture is poured into 750 ml of 2N HCl (pH value=1) and extracted three times with 300 ml of ether. The combined organic phases are dried over magnesium sulphate and concentrated on a rotary evaporator. The residue is treated with 200 ml of ether, the precipitated 2,5-bimethoxycarbonyl-1,4-cyclohexanedione is filtered off under suction and the filtrate is again concentrated. The crude product is column chromatographed on silica gel with ether/hexane 1:1 and gives 32.28 g (15.6%) of methyl 4-chloro-2-acetonylacetoacetate.

IR (liq. film): 3630-3400$^w$ (complex), 1750$^s$, 1715$^s$, 1660$^m$ cm$^{-1}$

NMR (CDCl₃)60 MHz: 2.20 (s/3H), 3.10–3.30 (m/2H), 3.78 (s/3H), 4.12–4.33 (m/1H), 4.50 (s/2H) ppm MS (m/e): 206 (M+), 175, 157, 125, 97, 87, 77, 49, 43 (100%).

(b) 6.20 g (30 mmol) of methyl 4-chloro-2-acetonylacetoacetate are held at reflux temperature for 1 hour with 63.6 g (15 mmol) of 2.5% Na₂CO₃ solution. The reaction mixture is poured into 30 ml of 1N HCl and extracted 3 times with 50 ml of CH₂Cl₂. The combined organic phases are dried over magnesium sulphate and concentrated on a rotary evaporator. The crude product is column chromatographed on silica gel with ether/hexane/CH₂Cl₂ 1:1:3 and gives 0.80 g (20.4%) of 2-chloro-3-methyl-2-cyclopenten-1-one, content 93.2%; m.p. 37°–39° C.

IR (CHCl₃): 1715$^s$, 1625$^s$ cm⁻¹
NMR (CDCl₃)60 MHz: 2.20 (s/3H), 2.60 (m/4H) ppm
MS (m/e): 130 (M+), 115, 102, 95, 67 (100%).

(c) 0.72 g (5.5 mmol) of 2-chloro-3-methyl-2-cyclopenten-1-one is stirred at room temperature for 1 hour with 27.5 ml (27.5 mmol) of 1N sodium hydroxide solution. The reaction mixture is brought to a pH value of 3 with concentrated hydrochloric acid and extracted 3 times with 20 ml of CH₂Cl₂. The combined organic phases are dried over magnesium sulphate and concentrated on a rotary evaporator. After recrystallization from ether/hexane 1:1 there is obtained 0.47 g (76.3%) of 2-hydroxy-3-methyl-2-cyclopenten-1-one; m.p. 101°–102° C.

IR (CHCl₃): 3500$^m$, 3310$^w$ (broad), 1710$^s$, 1660$^s$ cm⁻¹
NMR (CDCl₃)60 MHz: 2.62 (s/3H), 2.45 (s/4H), 5.80 (s, broad/1H) ppm
MS (m/e): 112 (M+, 100%), 97, 84, 69, 55, 41.

EXAMPLE 4

(a) See Example 1(a).

(b) 16.58 g (120 mmol) of potassium carbonate and 0.46 g (2 mmol) of benzyltriethylammonium chloride are suspended in 50 ml of acetonitrile. While stirring there are added thereto 14.60 g (100 mmol) of methyl 4-methoxyacetoacetate and there are added dropwise thereto within 10 minutes 15.97 g (150 mmol) of 3-chloro-2-butanone. The mixture is stirred at 20°–25° C. for a further 65 hours. The reaction mixture is poured on to 70 ml of 4N HCl/ice (pH value=1) and extracted 3 times with 100 ml of ethyl acetate each time. The combined organic phases are dried over magnesium sulphate and concentrated on a rotary evaporator. The crude product distils at 95° C./0.05 mbar and gives 6.67 g (42%) of methyl 4-methoxy-2-[1-methylacetonyl]-acetoacetate.

IR (liq. film): 3620–3400$^w$ (broad), 1745$^s$, 1715$^s$, 1635$^w$ cm⁻¹
NMR (CDCl₃)60 MHz: 1.08+1.16 (2d/3H), 2.20+2.23 (2s/3H), 3.15–3.55 (m/1H), 3.41+3.44 (2s/3H), 3.85–4.06 (m/1H), 4.18+ 4.21 2s/2H) ppm
MS (m/e): 216 (M+), 171, 139, 111, 69, 45 (100%).

(c) 2.16 g (10 mmol) of methyl 4-methoxy-2-[1-methylacetonyl]-acetoacetate are held at reflux temperature for 2 hours with 21.2 ml (5 mmol) of 2.5% Na₂CO₃ solution. The reaction mixture is extracted 3 times with 25 ml of CH₂Cl₂ each time. The combined organic phases are dried over magnesium sulphate and concentrated on a rotary evaporator to give 1.40 g (100%) or 2-methoxy-3,4-dimethyl-2-cyclopenten-1-one, content 96%.

IR (liq. film): 1700$^s$, 1640$^s$ cm⁻¹
NMR (CDCl₃)60 MHz: 1.19 (d/3H), 1.96 (s/3H), 1.72–2.83 (m/3H), 4.91 (s/3H) ppm.

(d) 0.70 g (5 mmol) of crude 2-methoxy-3,4-dimethyl-2-cyclopenten-1-one is held at reflux temperature for 3 hours with 7 g (10 fold amount by weight) of 5N hydrochloric acid. The reaction mixture is extracted 3 times with 50 ml of CH₂Cl₂ each time. The combined organic phases are dried over magnesium sulphate and concentrated on a rotary evaporator to give 0.45 g (71.4%) of 2-hydroxy-3,4-dimethyl-2-cyclopenten-1-one, content 90.6%. The data for this material are:

IR (CHCl₃): 3500$^m$, 3310$^w$ (broad), 1710$^s$, 1660$^s$ cm⁻¹
NMR (CDCl₃)60 MHz: 1.19 (d/3H), 1.99 (s/3H), 1.76–2.83 (m/3H), 6.02 (s, broad/1H) ppm.

The compound can be purified in accordance with Example 1.d).

Unless noted to the contrary, the content determinations were effected by gas chromatography.

Unless noted to the contrary, the IR, NMR and MS data were determined on purified material, for example material purified by crystallization or distillation.

EXAMPLE 5

(a) 1.66 g (12 mmol) of potassium carbonate and 0.04 g (0.2 mmol) of benzyltriethylammonium chloride are suspended in 5 ml of acetonitrile. While stirring there are added thereto 1.60 g (10 mmol) of methyl 4-methoxy-2-methylacetoacetate and there are then added dropwise thereto within 15 minutes 1.39 g (15 mmol) of chloroacetone. The mixture is stirred at 20°–25° C. for a further 21 hours. The reaction mixture is poured into 20 ml of 2N HCl (pH value=1) and extracted 3 times with 20 ml of ethyl acetate each time. The combined organic phases are dried over sodium sulphate and evaporated on a rotary evaporator. The crude product distils at 95° C./0.03 mbar. There results 0.83 g (38.4%) of methyl 4-methoxy-2-acetonyl-2-methylacetoacetate.

IR (liq. film): 1745$^s$ (shoulder), 1720$^s$, 1630$^w$ cm⁻¹
NMR (CDCl₃)60 MHz: 1.45 (s/3H), 2.12 (s/3H), 3.15 (s/2H), 3.40 (s/3H), 3.71 (s/3H), 4.38 (s/2H) ppm
MS (m/e): 216 (M+), 184, 171, 143, 111, 45, 43, (100%).

(b) 5.40 g (25 mmol) of methyl 4-methoxy-2-acetonyl-2-methylacetoacetate are held at reflux temperature for 2½ hours with 106 ml (12.5 mmol) of 2.5% Na₂CO₃ solution. The reaction mixture is extracted 3 times with 150 ml of CH₂Cl₂ each time. The combined organic phases are dried over magnesium sulphate and concentrated on a rotary evaporator to give 2.66 g (76%) of 2-methoxy-3,5-dimethyl-2-cyclopenten-1-one, content: 96.7%.

IR (liq. film): 1705$^s$, 1650$^s$ cm⁻¹
NMR (CDCl₃)60 MHz: 1.18 (d/3H), 1.98 (s/3H), 1.80–3.00 (m/3H), 3.90 (s/3H) ppm.

(c) 2.15 g (15.36 mmol) of crude 2-methoxy-3,5-dimethyl-2-cyclopenten-1-one are held at reflux temperature for 2 hours with 21.50 g (=10 fold amount by weight) of 5N hydrochloric acid. The reaction mixture is extracted 3 times with 50 ml of CH₂Cl₂ each time. The combined organic phases are dried over magnesium sulphate and concentrated on a rotary evaporator. After recrystallization from ether/hexane 1:1 there are obtained 1.05 g (54.2%) 2-hydroxy-3,5-dimethyl-2-cyclopenten-1-one; m.p. 92°–93° C.

IR (CHCl₃): 3500$^m$, 3310$^m$ (broad), 1710$^s$, 1660$^s$ cm⁻¹
NMR (CDCl₃)60 MHz: 1.18 (d/3H), 2.00 (s,3H), 1.80–3.00 (m/3H), 6.40 (s,1H) ppm
MS (m/e): 126 (M+, 100%), 111, 98, 83, 79, 69, 55, 43.

EXAMPLE 6

(a) 15.2 g (110 mmol) of potassium carbonate and 0.46 g (2 mmol) of benzyltriethylammonium chloride are suspended in 100 ml of acetonitrile. While stirring there are added thereto 20.2 g (100 mmol) of methyl 4-methoxy-2-acetonylacetoacetate and the mixture is heated to 60° C. Within 100 minutes there are added dropwise thereto 18.7 g (120 mmol) of ethyl iodide and the mixture is stirred at 60° C. for a further 24 hours. The suspension is then poured into a solution of 6.9 g (50 mmol) of potassium carbonate in 300 ml of water and then heated at reflux for 3 hours. The cooled reaction mixture is extracted 3 times with 100 ml of ether. The combined organic phases are dried over magnesium sulphate, concentrated on a rotary evaporator and thus give 12.92 g (84%) of 5-ethyl-2-methoxy-3-methyl-2-cyclopenten-1-one, content (GC): 97%. Boiling point 95° C./14 mbar.

IR (liq. film): 1700$^s$, 1645$^s$ cm$^{-1}$
NMR (CDCl$_3$)60 MHz: 0.95 (t/3H), 2.02 (s/3H), 1.4–2.9 (m/5H), 3.9 (s, 3H) ppm.

(b) 12.8 g (83 mmol) of crude 5-ethyl-2-methoxy-3-methyl-2-cyclopenten-1-one are held at reflux temperature for 2 hours with 128 g of 5N hydrochloric acid. The cooled reaction mixture is extracted 3 times with 100 ml of CH$_2$Cl$_2$. The combined phases are dried over magnesium sulphate and concentrated on a rotary evaporator. The crude product is distilled at 47°–48° C./0.03 mbar and yields 9.09 g (78.2%) of a mixture of 5-ethyl-2-hydroxy-3-methyl-2-cyclopenten-1-one (isomer A) and 3-ethyl-2-hydroxy-5-methyl-2-cyclopenten-1-one (isomer B) in the ratio of about 7:3, content (GC): isomer A 70.2%, isomer B 28.8%.

IR (CHCl$_3$): 3500$^m$, 330$^m$ (broad), 1705$^s$, 1655$^s$ cm$^{-1}$
NMR (CDCl$_3$)400 MHz: Isomer A: 0.95 (t/3H), 1.43 (m/1H), 1.82 (m/1H), 2.02 (s/3H), 2.12 (m/1H), 2.35 (m/1H), 2.60 (m/1H), 6.5 (s, broad/1H) ppm. Isomer B: 1.15 (t/3H), 1.18 (d/2H), 2.03 (m/1H), 2.43 (m/1H), 2.45 (q/2H), 2.71 (m/1H), 6.5 (s, broad/1H) ppm.
MS (m/e): 140 (M$^{30}$), 125, 112, 107, 97, 94 (100%).

EXAMPLE 7

(a) 15.20 g (110 mmol) of potassium carbonate and 0.46 g (2 mmol) of benzyltriethylammonium chloride are suspended in 100 ml of acetonitrile. While stirring there are added thereto 21.60 g (100 mmol) of methyl 4-methoxy-2-[1-methylacetonyl]-acetoacetate, the mixture is heated to 60° C. and 28.39 g (200 mmol) of methyl iodide are added dropwise thereto within 30 minutes. The mixture is stirred at 60° C. for a further 16 hours; then 6.91 g (50 mmol) of potassium carbonate and 7.10 g (50 mmol) of methyl iodide are again added and the mixture is stirred at 60° C. for a further 21 hours. 6.90 g (50 mmol) of potassium carbonate in 300 ml of distilled water are now added thereto. The reaction mixture is held at reflux temperature for 6 hours. It is then extracted 3 times with 100 ml of ether each time. The combined organic phases are dried over magnesium sulphate and concentrated on a rotary evaporator. The crude product distils at 70°–78° C./12 mm and yields 6.03 g (39.2%) of 2-methoxy-3,4,5-trimethyl-2-cyclopenten-1-one.

IR (liq. film): 1700$^s$, 1640$^s$ cm$^{-1}$
NMR (CDCl$_3$)60 MHz: 1.15 (d/6H), 1.92 (s/3H), 1.60–2.80 (m/2H), 3.88 (s/3H) ppm,
MS (m/e): 154 (M+), 139 (100%), 126, 111, 96, 79, 67, 55, 41.

(b) 5.39 g (35 mmol) of 2-methoxy-3,4,5-trimethyl-2-cyclopenten-1-one are held at reflux temperature for 90 minutes with 53.9 g (10 fold amount by weight) of 5N hydrochloric acid. The reaction mixture is extracted 3 times with 50 ml of ether each time. The combined organic phases are dried over magnesium sulphate and concentrated on a rotary evaporator. The crude product is distilled at 45°–48° C./0.03 mbar and yields 3.57 g (72.9%) of 2-hydroxy-3,4,5-trimethyl-2-cyclopenten-1-one.

IR (CHCl$_3$): 3500$^m$, 3310$^w$ (broad), 1710$^s$, 1660$^s$ cm$^{-1}$
NMR (CDCl$_3$)60 MHz: 1.15 (d/6H), 1.96 (s/3H), 1.60–2.80 (m/2H), 7.10 (s, broad/1H) ppm
MS (m/e): 140 (M+), 125 (100%) 112, 97, 83, 79, 69, 55, 43.

EXAMPLE 8

(a) 67.99 g (492 mmol) of potassium carbonate and 1.87 g (8.2 mmol) of benzyltriethylammonium chloride are suspended in 500 ml of acetonitrile. 59.86 g (410 mmol) of methyl 4-methoxyacetoacetate are added thereto while stirring. 65.50 g (615 mmol) of 1-chloro-2-butanone are added dropwise thereto within 30 minutes and the mixture is stirred at 20°–25° C. for 23 hours. The reaction mixture is poured into 1 l of 1N HCl (pH value=1) and extracted 3 times with 700 ml of ethyl acetate each time. The combined organic phases are dried over magnesium sulphate and concentrated on a rotary evaporator. The crude product distils at 115° C./0.05 mbar. There results 49.01 g (55.3%) of methyl 4-methoxy-2-(2-oxobutyl)-acetoacetate.

IR (liq. film): 1740$^s$, 1720$^s$, 1630$^m$ cm$^{-1}$
NMR (CDCl$_3$)60 MHz: 1.08 t/3H), 2.51 (q/2H), 3.12 (m/2H), 3.48 (s/3H), 3.78 (s/3H), 4.15 (m/1H), 4.30 (s/2H) ppm
MS (m/e): 216 (M+), 184, 171, 139, 57, 45 (100%).

(b) 21.60 g(100 mmol) of methyl 4-methoxy-2-(2-oxobutyl)-acetoacetate are held at reflux temperature for 8 hours with 212.0 g (50 mmol) of 2.5% Na$_2$CO$_3$ solution. After cooling the reaction mixture is extracted 3 times with 200 ml of CH$_2$Cl$_2$ each time. The combined organic phases are dried over magnesium sulphate and concentrated on a rotary evaporator. The crude product is column chromatographed over SiO$_2$ and gives 4.08 g (29.1%) of 3-ethyl-2-methoxy-2-cyclopenten-1-one.

IR (liq. film): 1700$^s$, 1635$^s$ cm$^{-1}$
NMR (CDCl$_3$)60 MHz: 1.13 (t/3H), 2.43 (s/4H), 2.46 (q/2H), 3.93 (s/3H) ppm
MS (m/e): 140 (M+, 100%), 125, 111, 97, 69.

(c) 3.08 g (22 mmol) of 3-ethyl-2-methoxy-2-cyclopenten-1-one are held at reflux temperature for 5 hours with 30.80 g of 5N hydrochloric acid. After cooling the reaction mixture is extracted 3 times with 50 ml of CH$_2$Cl$_2$ each time. The combined organic phases are dried over magnesium sulphate and concentrated on a rotary evaporator. The crude product is bulb-tube distilled at 0.1 mbar/110° C. and gives 1.82 g (65.7%) of 3-ethyl-2-hydroxy-2-cyclopenten-1-one (melting point 39°–41° C.).

IR (CHCl$_3$): 3500$^m$, 3310$^m$ (broad), 1710$^s$, 1660$^s$ cm$^{-1}$
NMR (CDCl$_3$)60 MHz: 1.13 (t/3H), 2.43 (s/4H), 2.46 (q/2H), 6.60 (s, broad/1H) ppm,
MS (m/e): 126 (M+, 100%), 111, 77, 83, 69, 55, 43.

EXAMPLE 9

(a) 22.80 g (165 mmol) of potassium carbonate and 0.69 g (3 mmol) of benzyltriethylammonium chloride are suspended in 150 ml of acetonitrile. While stirring 32.42 g (150 mmol) of methyl 4-methoxy-2-(1-methylacetonyl)-acetoacetate are added thereto and the mixture is heated to 60° C. 28.08 g (180 mmol) of ethyl iodide are added thereto within 100 minutes and the mixture is stirred at 60° C. for a further 90 hours. The suspension is then poured into a solution of 10.35 g (75 mmol) of potassium carbonate in 450 ml of water and heated at reflux temperature for 30 hours. The cooled reaction solution is extracted 3 times with 300 ml of $CH_2Cl_2$. The combined organic phases are dried over magnesium sulphate and concentrated on a rotary evaporator. The crude product is distilled at 20 mbar/9-7°-99° C. and gives 3.61 g (14.3%) of 5-ethyl-2-methoxy-3,4-dimethyl-2-cyclopenten-1-one.

IR (liq. film): $1700^s$, $1640^2$ $cm^{-1}$

NMR ($CDCl_3$)60 MHz: 0.82–1.10 (m/3H), 2.20 (d/3H), 1.94 (s/3H), 1.32–2.61 (m/4H), 3.93 (s/3H) ppm MS (m/e): 168 ($M^+$), 153, 140, 125, 108 (100%), 93, 55.

(b) 2.06 g (12.2 mmol) of 5-ethyl-2-methoxy-3,4-dimethyl-2-cyclopenten-1-one are held at reflux temperature for 2 hours with 20.6 g of 5N hydrochloric acid. The cooled reaction solution is extracted 3 times with 50 ml of $CH_2Cl_2$. The combined organic phases are dried over magnesium sulphate and concentrated on a rotary evaporator. The crude product is bulb-tube distilled at 1 mbar/104° C. and gives 1.43 g (76.1%) of a mixture of 5-ethyl-2-hydroxy-3,4-dimethyl-2-cyclopenten-1-one (isomer A) and 3-ethyl-2-hydroxy-4,5-dimethyl-2-cyclopenten-1-one (isomer B) in the ratio of about 4:1. Content (GC): isomer A 68.9%, isomer B 17.1%.

IR (liq. film): $3500^m$, $3300^m$ (broad), $1705^s$, $1655^s$ $cm^{-1}$

NMR ($CDCl_3$): 0.82–1.10 (m/about 3H), 2.20 (d/about 4H), 1.99 (s/about 3H), 1.32–2.92 (m/about 3H), 6.61 (s, broad/1H) ppm MS (m/e): 154 ($M^+$), 139, 126, 108, 55, 43 (100%).

In the following Examples "compound I" stands for the novel 2-hydroxy-3,4,5-trimethyl-2-cyclopenten-1-one.

EXAMPLE 10

An almond-hazelnut flavour can be made up as follows:

|  | Parts by weight | |
|---|---|---|
| Vanillin | 25.0 | 25.0 |
| Acetylpyrazine | 2.5 | 2.5 |
| Diacetyl | 3.0 | 3.0 |
| Dimethylresorcinol | 3.0 | 3.0 |
| Furfural | 4.0 | 4.0 |
| Benzaldehyde | 8.0 | 8.0 |
| gamma-Nonalactone | 1.0 | 1.0 |
| Trimethylpyrazine | 1.0 | 1.0 |
| Propylene glycol | 922.5 | 946.5 |
| Corylone | 30.0 | — |
| Compound I | — | 6.0 |
|  | 1000.0 | 1000.0 |

Dosage in a milk drink: 50 gr/100 liter (an analogous dosage applies for a maple, chocolate and coffee flavour, etc.).

In flavours the novel compound I produces sensorically the same effect as about a 5-fold amount of "Corylone". (As mentioned above, the novel compound, quite apart from the flavour intensity examined here, is even 20 times stronger).

EXAMPLE 11

(a)

| Tobacco base | Parts by weight |
|---|---|
| o-tert.Butylcyclohexyl acetate | 400 |
| Jasmin oil synth. | 300 |
| Musk ketone | 40 |
| Sandela Givaudan | 40 |
| Styrallyl acetate | 30 |
| Coumarin | 20 |
| Isobutylquinoline 10% DPG (dipropylene glycol) | 10 |
| Lavender oil | 10 |
| Vetiver oil | 10 |
| Galbanum oil | 10 |
| Vassura oil | 10 |
| DPG | 40 |
|  | 920 |

If 10 parts of a 10% solution in ethanol of the compound I is added to the above base, then the composition receives a pleasant warmth; its sweet jasmin note is supplemented by a fresh-herby note.

(b)

| Leather base | Parts by weight |
|---|---|
| Sytrax nat. RIFM | 250 |
| Castoreum anhydrous | 150 |
| Bergamot oil | 100 |
| Musk inf. 3% in ethanol | 100 |
| Vetiver oil | 100 |
| Labdanum resinoid | 100 |
| Birch tar oil dephenolized 10% DPG | 50 |
| Musk ketone | 25 |
| Sandalwood oil | 10 |
| Vanillin | 5 |
| Ciste labdanum | 5 |
| DPG | 60 |
|  | 960 |

If a 10% solution of the compound I is added to the above base, then the leather base surprisingly gains a strong smoky note which combines very well with the leather character of the base and supplements this harmonically without the birch tar oil appearing in an unpleasant manner.

(c)

| Fougere base | Parts by weight |
|---|---|
| Lavender oil | 200 |
| Linalyl acetate | 150 |
| Tree moss absolute | 60 |
| Coumarin | 50 |
| Patchouli oil | 30 |
| Rhodinol extra ex geranium oil | 30 |
| Methyl dihydrojasmoate | 30 |
| Musk ketone | 30 |
| Vetivenyl acetate | 30 |
| Geranium BB synth. | 30 |
| Amyl salicylate | 20 |
| Sandela Givaudan | 20 |
| Linalool | 20 |
| Benzyl acetate | 15 |
| Ylang-ylang oil | 15 |
| Eugenol | 15 |

| Fougere base | |
|---|---|
| | Parts by weight |
| Thyme oil | 5 |
| DPG | 50 |
| | 800 |

If 10 parts of a 10% solution of the compound I are added to the above base, then the herby note of the fougère base is underlined in a pleasant manner and the lavender note is rounded-off finely.

(d)

| Rose base | |
|---|---|
| | Parts by weight |
| Phenylethyl alcohol | 300 |
| Geraniol | 250 |
| Jasmin "lavage" | 200 |
| Citronellol extra | 100 |
| alpha-Ionone | 40 |
| C-10-Aldehyde 10% DPG | 5 |
| C-11-Aldehyde 10% DPG | 5 |
| | 900 |

If 10 parts of a 10% solution of the compound I are added to this base, then the composition takes on a novel, interesting direction; it now becomes very much more sharp, but without losing in naturalness.

In the above Example the compound I was, moreover, in each instance replaced by the same amount of the known 2-hydroxy-3,4,4-trimethyl-2-cyclopenten-1-one. In all of these cases a negative effect was achieved. In all cases an unpleasant lovage note of the known trimethyl derivative pervaded, which conferred to the composition an undesired "food note".

I claim:

1. A compound of the formula

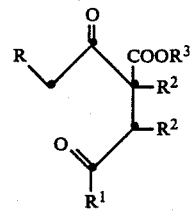

wherein:
R represents $C_{1-4}$-alkoxy, chlorine, bromine or $C_{1-4}$-alkanoyloxy, $R^1$ signifies $C_{1-5}$-alkyl, the radicals $R^2$ each independently represent hydrogen or $C_{1-5}$-alkyl, and $R^3$ signifies $C_{1-4}$-alkyl.

2. A compound according to claim 1 wherein:
(a) $R^1$ is selected from the group consisting of methyl, ethyl, propyl and isopropyl, and,
(b) $R^2$ is selected from the group consisting of hydrogen, methyl, ethyl, propyl and isopropyl.

3. A compound according to claim 2 which is Methyl 4-methoxy-2-acetonylacetoacetate.

4. A compound according to claim 2 which is Methyl 4-acetoxy-2-acetonylacetoacetate.

5. A compound according to claim 2 which is Methyl 4-chloro-2-acetonylacetoacetate.

6. A compound according to claim 2 which is Methyl 4-methoxy-2-(1-methylacetonyl)-acetoacetate.

7. A compound according to claim 2 which is Methyl 4-methoxy-2-acetonyl-2-methyl-acetoacetate.

8. A compound according to claim 2 which is Methyl 4-methoxy-2-(2-oxobutyl)-acetoacetate.

* * * * *

UNITED STATES PATENT AND TRADEMARK OFFICE
CERTIFICATE OF CORRECTION

PATENT NO. : 4,892,966

DATED : January 9, 1990

INVENTOR(S) : Hans J. Wild

It is certified that error appears in the above-identified patent and that said Letters Patent is hereby corrected as shown below:

In column 2, the Reaction Scheme, compound IV, correct

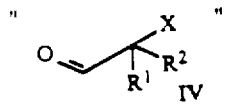

to read

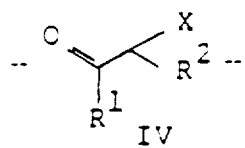

Signed and Sealed this

Fourth Day of February, 1992

Attest:

HARRY F. MANBECK, JR.

Attesting Officer      Commissioner of Patents and Trademarks